US011273440B2

(12) United States Patent
Weinstock et al.

(10) Patent No.: US 11,273,440 B2
(45) Date of Patent: Mar. 15, 2022

(54) SEPARATOR (71) Applicant: SARSTEDT AKTIENGESELLSCHAFT & CO.KG, Nümbrecht (DE)

(72) Inventors: Mark Weinstock, Helmenzen (DE); Christian Wegener, Nümbrecht (DE); Ulrich Karrenberg, Marienheide (DE)

(73) Assignee: SARSTEDT AKTIENGESELLSCHAFT & CO. KG, Nümbrecht (DE)

( * ) Notice: Subject to any disclaimer, the term of this patent is extended or adjusted under 35 U.S.C. 154(b) by 213 days.

(21) Appl. No.: 16/608,738

(22) PCT Filed: Apr. 25, 2018

(86) PCT No.: PCT/EP2018/060601
§ 371 (c)(1),
(2) Date: Oct. 25, 2019

(87) PCT Pub. No.: WO2018/197564
PCT Pub. Date: Nov. 1, 2018

(65) Prior Publication Data
US 2021/0283599 A1 Sep. 16, 2021

(30) Foreign Application Priority Data
Apr. 26, 2017 (DE) .................. 10 2017 108 935.7

(51) Int. Cl.
B01D 21/26 (2006.01)
B01L 3/00 (2006.01)

(52) U.S. Cl.
CPC ........ B01L 3/50215 (2013.01); B01D 21/262 (2013.01); B01L 2400/0633 (2013.01)

(58) Field of Classification Search
CPC ..................... B01L 3/50215; B01L 2400/0633
(Continued)

(56) References Cited

U.S. PATENT DOCUMENTS 3,887,464 A    6/1975 Ayres
4,088,582 A *   5/1978 Murty ................. B01L 3/50215
                                                                               210/516

(Continued)

FOREIGN PATENT DOCUMENTS

DE    60023823    8/2006
DE    69931584    5/2007
(Continued)

Primary Examiner — Nina Bhat
(74) Attorney, Agent, or Firm — Smartpat PLC (57) ABSTRACT

A separator separates a first from a second phase of a liquid in a tubular container. The separator has a float made of elastic material having a circumferential sealing edge and at least one ballast fastened to the underside of the float. The density of the ballast is greater than the density of the float and the density of the entire separator lies in a value range between the density of the first phase and the density of the second phase of the liquid. In order to securely prevent penetration of parts of the second phase of the liquid into the region above the separator within the tubular container, when the separator moves into the sealing position and is positioned there, the sealing edge of the float is formed at a predetermined distance greater than zero above the center of gravity of the entire separator.

9 Claims, 5 Drawing Sheets a)

b)

(58) Field of Classification Search
USPC .............. 422/533; 210/516, 515, 518, 513
See application file for complete search history.

(56) References Cited

U.S. PATENT DOCUMENTS

| | | | |
|---|---|---|---|
| 4,443,345 A | 4/1984 | Wells | |
| 4,843,869 A | 7/1989 | Levine et al. | |
| 5,632,905 A | 5/1997 | Haynes | |
| 6,280,400 B1* | 8/2001 | Niermann | B01L 3/50215 600/573 |
| 6,406,671 B1* | 6/2002 | DiCesare | B01L 3/50215 210/512.1 |
| 6,409,528 B1 | 6/2002 | Bodnar | |
| 6,479,298 B1* | 11/2002 | Miller | B01L 3/50215 210/121 |
| 6,537,503 B1* | 3/2003 | Conway | B01L 3/50215 210/789 |
| 7,188,734 B2* | 3/2007 | Konrad | B01L 3/5021 210/513 |
| 8,998,000 B2* | 4/2015 | Crawford | B01D 17/0217 210/512.1 |
| 9,333,445 B2* | 5/2016 | Battles | B01D 21/0084 |
| 9,731,290 B2* | 8/2017 | Crawford | B01D 17/0217 |
| 9,919,307 B2* | 3/2018 | Crawford | B01L 3/50215 |
| 9,919,308 B2* | 3/2018 | Crawford | B01D 21/2405 |
| 10,376,879 B2* | 8/2019 | Crawford | B01L 3/50215 |
| 10,413,898 B2* | 9/2019 | Crawford | B01D 21/2405 |
| 10,456,782 B2* | 10/2019 | Crawford | G01N 1/34 |
| 10,807,088 B2* | 10/2020 | Crawford | G01N 1/34 |
| 2002/0094305 A1 | 7/2002 | DiCesare et al. | |
| 2002/0132367 A1 | 9/2002 | Miller et al. | |
| 2002/0156439 A1* | 10/2002 | Iskra | B01L 3/5082 604/317 |
| 2004/0256331 A1* | 12/2004 | Arking | B01L 3/563 210/787 |
| 2005/0059163 A1* | 3/2005 | Dastane | A61B 5/150351 436/177 |
| 2010/0288694 A1* | 11/2010 | Crawford | B01D 17/0217 210/521 |
| 2011/0036786 A1 | 2/2011 | Ellsworth | |
| 2013/0315798 A1 | 11/2013 | Crawford et al. | |
| 2016/0136640 A1 | 5/2016 | Losada et al. | |

FOREIGN PATENT DOCUMENTS

| | | | | |
|---|---|---|---|---|
| EP | 0017127 A2 | 10/1980 | | |
| EP | 0098150 A2 | 1/1984 | | |
| EP | 0753741 A1 | 1/1997 | | |
| EP | 1106252 A2 | 6/2001 | | |
| JP | H09222427 A | 8/1997 | | |
| WO | 2009073232 A1 | 6/2009 | | |
| WO | WO-2009073232 A1 * | 6/2009 | ......... | B01L 3/50215 |
| WO | 2010132783 A1 | 11/2010 | | |
| WO | 2014120678 A2 | 8/2014 | | |
| WO | 2016076911 A1 | 5/2016 | | |

* cited by examiner

SEPARATOR

TECHNICAL FIELD

The invention relates to a separator for separating a first phase from a second phase of a liquid in a tubular container. In particular, separators are meant to separate blood serum (the first phase) from cruor (the second phase) in blood (the liquid) within a blood collection tube. The invention also relates to the tubular container.

BACKGROUND

Blood collection tubes having separators are generally known in the prior art. In a delivery state the separators are fixed in an initial position of the blood collection tubes. When blood flows into the blood collection tube via an inlet, it flows around or through the separator; in any case, in the initial position, the separator does not constitute a seal for the blood within the blood collection tube. For medical analysis it is necessary for the blood to be separated into two components, namely blood serum and cruor. For this purpose, the blood collection tube with the blood located therein is centrifuged. The heavier cruor then settles due to centrifugation in the volume region near the bottom of the blood collection tube, while the lighter blood serum floats on the cruor. The separator detaches from its initial position and moves into a sealing position under the action of the centrifugal force. Because the density of the entire separator lies in a value range between the density of the blood serum and the density of the cruor, the separator automatically positions itself exactly at the phase boundary between blood serum and cruor. This position is also referred to as sealing position, because in this position, the separator rests with its sealing edge circumferentially against the inner side of the tubular sample tube in a sealing manner and thus separates the blood serum from the cruor. The separator maintains this sealing position even after the end of centrifugation so that the blood serum and the cruor are separately available for a laboratory examination.

Separators are disclosed, for example, in international patent application WO 2010/132783 A1. The separators described therein each have a float made of elastic material having a sealing edge that is circularly circumferential in top view, wherein, in a sealing position, the sealing edge is designed for resting against the inner side of a tubular sample container in a sealing manner. A ballast is fastened in each case to the underside of the float. The density of the ballast is in each case greater than the density of the float and the density of the entire separator lies in a value range between the density of the first phase and the density of the second phase of the liquid.

Depending on the design of the separator in the prior art, when the separator moves into the sealing position, but before it has reached said sealing position, small amounts of the second phase of the liquid can disadvantageously reach into the region above the separator in the tubular container and mix with the first phase of the liquid there.

The prior art in the form of document WO 2016/076911 A1 discloses a separation unit for separating a liquid into a first light phase and a second heavier phase using centrifugal force, wherein the liquid can be blood. A tubular container has a separator, wherein the separator has a float in the upper region and a ballast in the lower region. The separator is designed for resting against the inner side of the tubular container in a sealing manner. The density of the ballast in this case is greater than the density of the float and the density of the separator lies between the density of the first phase and the density of the second phase of the liquid to be separated.

Document DE 699 31 584 T2 describes a device for separating a fluid sample under centrifugal force into a phase having a higher specific gravity and a phase having a lower specific gravity, wherein the fluid sample can be a blood sample. The device has a separator element (separator) which is arranged in a cylindrical tube. The separator element has a float in the upper region and a ballast element in the lower region and a sealing body resting against the inner side of the tube in a sealing manner. The density of the ballast in this case is greater than the density of the float and the entire density of the separator lies between the density of the first phase and the density of the second phase of the liquid to be separated.

Document DE 600 23 823 T2 discloses a device for separating a liquid sample (for example, blood) into a first phase of high density and into a phase of low density under the action of centrifugal force. A separator is arranged in a tube having a cylindrical side wall, which separator has a float in the upper region and a ballast part in the lower region and a bellows for resting against the inner side of the tube in a sealing manner. The density of the ballast part in this case is greater than the density of the float and the entire density of the separator lies between the densities of the first phase and the second phase of the liquid to be separated.

Document U.S. Pat. No. 5,632,905 A relates to the separation of a blood sample into a lighter and a heavier phase by centrifuging in a tube. A separator is arranged in the tube. The separator has a disk-like shape and rests in a sealing position against the phase boundary between lighter and heavier phase.

SUMMARY

The invention has the object to further improve a known separator for separating a first from a second phase of a liquid in a tubular container and a corresponding known container such that a penetration of parts of the second phase of the liquid into the region above the separator within the tubular container is securely prevented when the separator moves into the sealing position and is positioned there.

This object is achieved with regard to the separator by the subject matter as claimed. The separator is characterized in that the sealing edge of the float is arranged at a predetermined distance greater than zero above the center of gravity of the entire separator.

In general: The density of the second phase of the liquid is greater than the density of the first phase of the liquid. For blood as a liquid, this means that the cruor as the second phase has a greater density than the blood serum, which corresponds to the first phase. The blood serum therefore floats on the cruor after a centrifugation. The density of the entire separator lies in a value range between the density of the first phase and the density of the second phase of the liquid. Therefore, the separator always positions itself in the sealing position on the phase boundary between the two phases.

Unless otherwise stated, the separator is described in the following in a normal position. The ballast is arranged below the float in this normal position. The center of gravity of the float, the center of gravity of the ballast and the center of gravity of the entire separator all lie on a vertical line, wherein the center of gravity of the entire separator lies between the centers of gravity of the float and the ballast. The terms used in the following, such as vertical, horizontal, below, above, side view and top view, etc., all refer to this normal position. The sealing position corresponds to the normal position where the tubular container is vertical.

In the delivery state, respectively in its initial position, the separator is detachably clamped in the tubular container. Under the action of a force, in particular the centrifugal force, the separator detaches from this initial position and moves into the sealing position described above. In this case it turns by 90°. Because the density of the entire separator lies, as said, between the density of the first phase and the density of the second phase of the liquid, the separator exactly positions itself in the sealing position so that its entire center of gravity lies on the phase boundary, that is, for example, between blood serum and cruor.

In order to prevent even small amounts of the second phase of the liquid reaching the region above the separator and thus the first phase of the liquid, just before the separator has assumed the sealing position, the sealing edge of the float is formed at a predetermined distance greater than zero above the center of gravity of the entire separator. The greater this distance, the more securely a mixing of the first and the second phase above the separator is prevented. This is important for the medical analysis of, in particular, the first phase of the liquid, that is, the blood serum.

According to a first embodiment, the distance lies, for example, in a range between 0.05 mm and 4 mm, but preferably in a range between 1 mm and 3 mm. The selected distance from this range represents a compromise. As said, on the one hand, it must have a certain minimum size to securely prevent the otherwise imminent mixing of the first and second phase; on the other hand, it should not be chosen too large, because otherwise too much of the first phase of the liquid is lost and is no longer available for medical analysis. The lost amount of the first phase is that residual quantity which, after positioning of the separator in the sealing position, is located or set below the sealing edge of the separator and above the phase boundary.

Depending on the configuration of the separator and in particular of its float, the sealing edge, viewed in a side view, is designed extending straight and horizontal in the circumferential direction or, however, extending wave-shaped. In the latter case, the distance is measured from the deepest wave trough to the center of gravity of the entire separator.

The technical teaching of the present invention applies to any shaped separator. In particular, it applies both to separators whose floats are disk-shaped, are designed with spherical deformation or without spherical deformation, and for spherical or cup-shaped separators. Likewise, it also applies to separators having ballast bodies of any shape. Thus, it applies in particular to ballast bodies which are designed in the shape of a plurality of fingers which extend away from the underside of a disk-shaped float.

The object of the invention mentioned above is achieved with respect to the tubular container by the subject matter as claimed. The advantages of this solution correspond to the advantages mentioned above with respect to the separator.

DETAILED DESCRIPTION

The invention is described in detail in the following with reference to said figures in the form of exemplary embodiments. The same technical elements are designated by the same reference numerals in all figures.

FIGS. 1a and 1b shows a separator 100 according to a first embodiment in a perspective view and in a side view. Its float 110 is generally disk-shaped, but it is spherically deformed. Therefore, the circumferential edge 112 is formed wave-shaped with wave troughs 118 and wave crests 117 when viewed from the side. Ballast bodies 120 stick out in the shape of fingers 124 downward from the underside of the disk-shaped float 110 in each case in the region of the wave troughs 118. Material accumulations on the upper side of the disk-shaped float are preferably designed from the material of the float in the region of the wave crests 117; these accumulations act as additional buoyancy bodies 113. In the embodiment shown in FIGS. 1a and 1b, the fingers 124 and the buoyancy bodies 113 are respectively arranged alternately distributed at a circumferential angular distance of $\varphi=90°$ at the periphery of the disk-shaped float.

Figure 1:
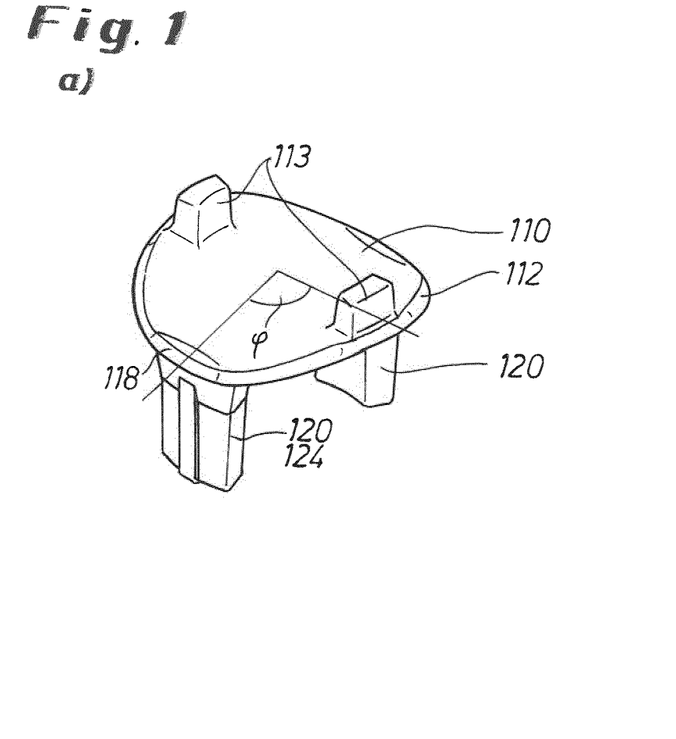
FIGS. 1a and 1b show a separator having disk-shaped float according to a first embodiment.
Figure 2:
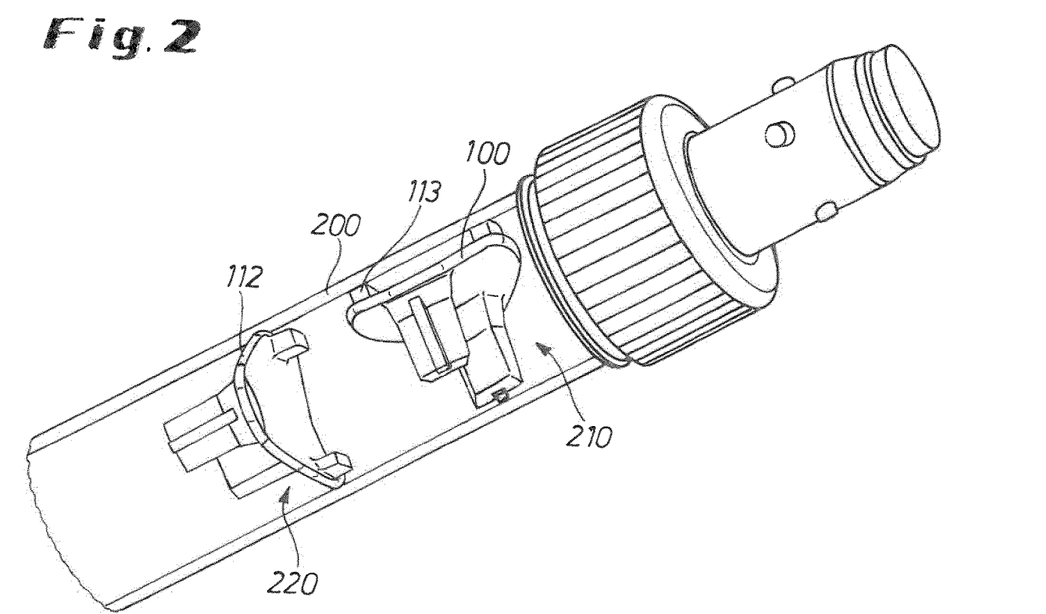
FIG. 2 shows the separator according to FIGS. 1a and 1b in a tubular container.

FIG. 2 shows the separator according to FIGS. 1a and 1b in the interior of the tubular container 200. In the delivery state the separator is located in its initial position 210. It is then propped up against the inner side of the tubular container 200 on the one side with the free ends of the fingers 124 and on the other side with the free ends of the buoyancy bodies 113. The free ends of the buoyancy bodies 113 are therefore preferably rounded in accordance with the inner radius of the tubular container 200. In the initial position 210, blood flowing into the tubular container can flow around the separator 100, so that the blood can also reach deeper volume regions of the tubular container.

Under the action of a force, in particular the centrifugal force, the separator 100 is detached from its initial position 210 and moves into a sealing position 220. At the same time it turns by 90°. The separator 100 deforms back into its starting state only when it is no longer under the action of the centrifugal force. Its sealing edge 112, in the sealing position 220 in the circumferential direction R, rests everywhere against the inner side of the tubular container 200 in a sealing manner and in this way, separates the two phases of the liquid or the blood effectively from each other.

Figure 3:
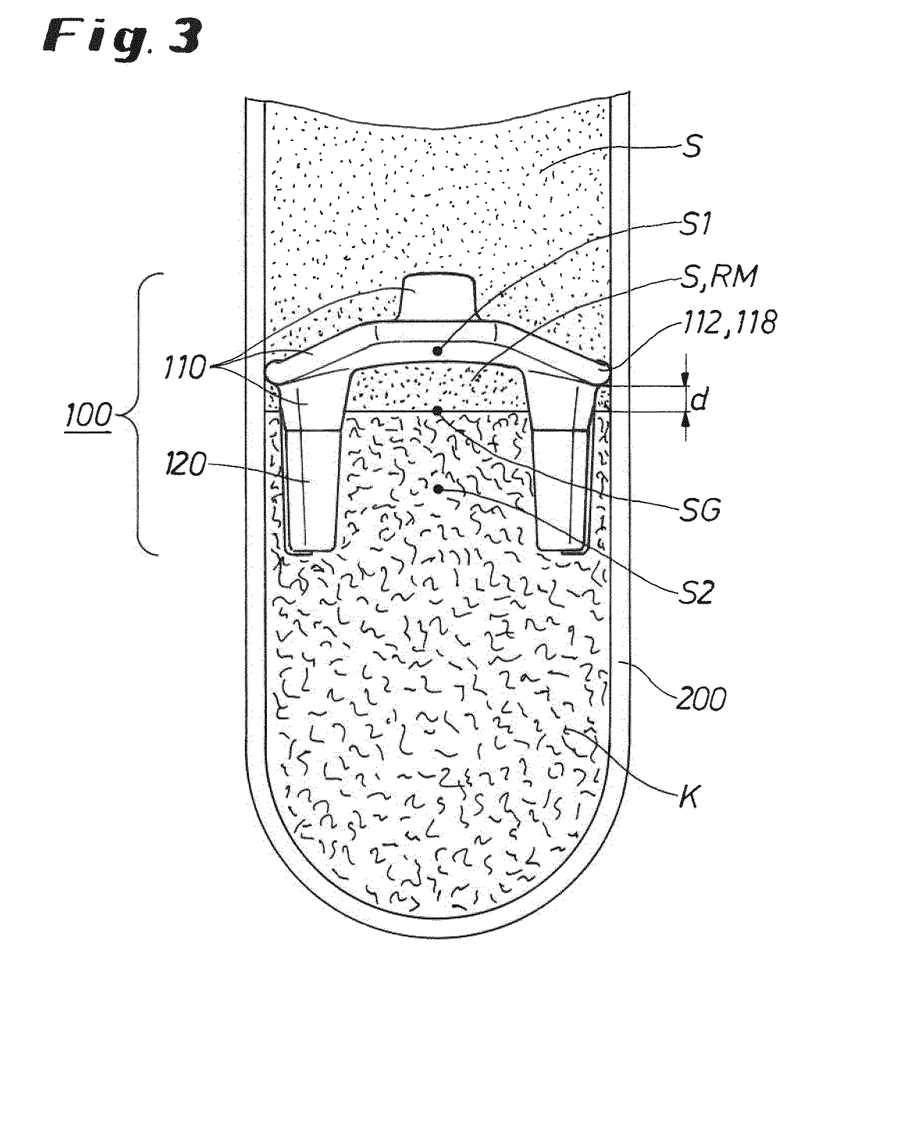
FIG. 3 shows an enlarged detail illustration of FIG. 2.

FIG. 3 shows an enlarged detail from FIG. 2. Specifically, FIG. 3 shows the separator 100 in the sealing position within the tubular container 200. The reference characters S1 designates the center of gravity of the float 110; reference characters S2 designates the center of gravity of the ballast 120. The center of gravity of the entire separator 100 is designated by the reference character SG.

FIG. 3 shows the vertical container 200 having liquid located therein after centrifugation. The liquid, for example, blood, has separated into two phases due to the centrifugation. The density of the first phase, for example, blood serum S, is less than the density of the second phase, for example, cruor K. The first phase having the lower density therefore floats on the second heavier phase after centrifugation. This is shown in FIG. 3. There, the lighter blood serum floats on the heavier cruor.

The density of the entire separator 100 lies in a value range between the density of the first phase and the density of the second phase of the liquid or of the blood. Therefore, in the sealing position shown, the separator 100 in FIG. 3 is automatically positioned so that its entire center of gravity SG lies exactly at the phase boundary between the first and the second phase of the liquid.

As explained above, the sealing edge 112 of the separator or the float 110 has a predetermined distance d to the center of gravity SG of the entire separator. This distance d, also called security distance, should not be chosen, as explained above, on the one hand, too large, but on the other hand, also not too small. If it is chosen too small, there is a risk that the first phase of the liquid above the separator is contaminated by portions of the second phase K, while the separator 100 moves into the sealing position. On the other hand, when it is chosen too large, too much of the first phase of the liquid will be lost; this is the residual amount RM at the first phase of the liquid which accumulates between the sealing edge 112 of the separator in the sealing position and the phase boundary. This residual amount RM is no longer available for the medical analysis of the first phase of the liquid. This distance d lies, for example, within a range of 0.05 mm to 4 mm, preferably between 1 mm and 3 mm. The distance d is basically always measured from the lower edge of the sealing edge 112 to the phase boundary. In the wave-shaped sealing edge, as shown in FIG. 3, it is measured from the deepest wave trough 118 of the sealing edge up to the center of gravity SG of the entire separator, respectively up to the phase boundary.

It is important that the technical teaching of the invention just described applies to any separator. It applies in particular not only to the separator according to the first embodiment of the invention, as shown in FIGS. 1 to 3.

Further possible separators are shown in the following FIGS. 4 to 7; these are briefly described in the following; however, as stated, the technical teaching of the invention is not limited to these embodiments of the separator.

Figure 4:
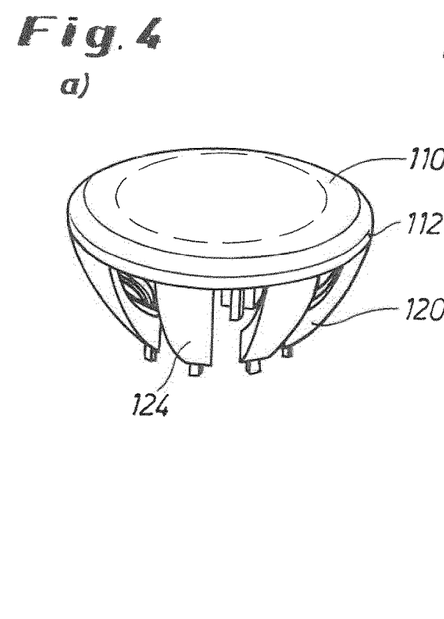
FIG. 4 shows a separator according to a second embodiment.

FIG. 4 shows the separator 100 according to a second embodiment in a perspective view and in a cross-sectional representation. The separator 100 consists of a float 110 and a ballast 120. The float 110 is designed disk-shaped having a bulge as a buoyancy body 113 in its center and having a circumferential sealing edge 112. The ballast 120 is designed in the form of a plurality of fingers 124 which extend away from the underside of the disk-shaped float 110. The fingers 124 are arranged distributed on the edge of the ballast.

Figure 5:
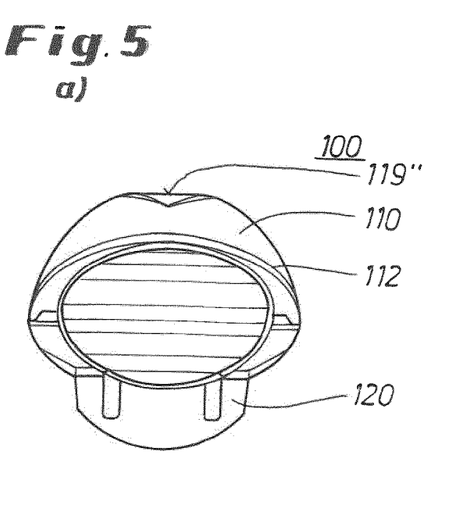
FIG. 5 shows a separator according to a third embodiment.

FIG. 5 shows the separator 100 in a spherical configuration (3rd embodiment). It consists of the elastic float 110 having the sealing edge 112 that is circular in top view. This does not stand in the way of the sealing edge 112 being formed wave-shaped in the side view of FIG. 5. Reference numeral 118 designates a wave trough of the sealing edge 112. The distance d is measured from this wave trough downward to the center of gravity of the separator.

A ballast 120 is fastened to the underside of the float 110. The float 110 is locally narrowed according to FIG. 5. It is designed as a membrane 116 in the region of the narrowing 114. The membrane is designed wave-shaped with wave crests and wave troughs. Regardless thereof or alternatively, the membrane 116 could also be formed of elastic material. The formation of the membrane in wave shape and/or of elastic material is required to enable a spring action of the membrane. The membrane acts as a tension spring, whereby the float and the ballast are moved a bit closer to each other. The separator is widened as a result, in particular the float, with the result that, in the sealing position, the sealing edge presses with a sufficiently large pressure against the inner side of the container in order to effectively delimit the two phases of the liquid from each other.

The float 110 has a local flattening 119" or bead on its upper side facing away from the ballast 120. The float does not rest against the inner side of the container in a sealing manner in the initial position in the region of the flattening, and thus enables a local flow around the separator with the liquid flowing into the container.

Figure 6:
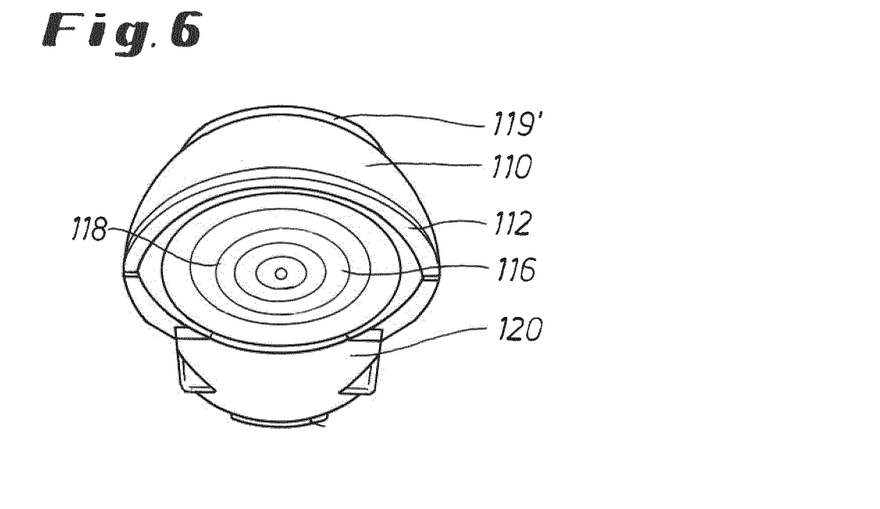
FIG. 6 shows a separator according to a fourth embodiment.

FIG. 6 shows the spherical separator 100 in a fourth embodiment. This embodiment substantially differs only in the shape of the membrane 116 and in the design of the surface of the float from the embodiment according to FIG. 5.

The wave crests and the wave troughs of the membrane 116 are also annular, but here they are designed oval. The upper side of the float 110 has an elevation 119' instead of the flattening. The flattening and the elevation equally cause residues of the liquid, in particular, blood residues, being unable to accumulate in their surroundings, which residues cannot escape between the separator and the wall of the container.

Figure 7:
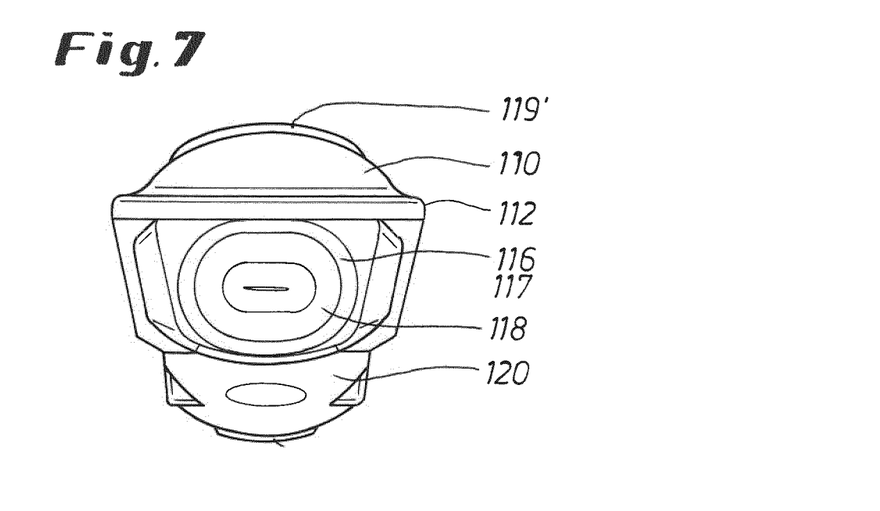
FIG. 7 shows a separator according to a fifth embodiment.

FIG. 7 shows the separator 100 in a fifth cup-shaped design. Apart from its outer (cup) shape, this separator substantially differs from the separator according to FIGS. 5 and 6 only in the circumferential sealing edge 112. The sealing edge 112 is not wave-shaped here, but designed to extend straight horizontally.

LIST OF REFERENCE NUMERALS 100 separator
110 float
112 sealing edge
113 buoyancy body/material bulge
116 membrane
117 wave crest
118 wave trough
119' elevation
119" flattening/bead
120 ballast
124 fingers
200 container
210 initial position
220 sealing position
d distance
K cruor, general second phase of the liquid
R circumferential direction
S blood serum, generally first phase of the liquid
S1 center of gravity of the float
S2 center of gravity of the ballast
SG center of gravity of the entire separator
RM residual amount
φ circumferential angular distance

The invention claimed is:

1. A separator (100) for separating a first phase from a second phase of a liquid under centrifugal force in a tubular container (200), comprising:
   a float (110) made of elastic material having a circumferential sealing edge (112) which rests against an inner side of the tubular container in a sealing manner (200) when the separator is in a sealing position (220); and
   at least one ballast (120) fastened to an underside of the float (110)
   wherein a density of a material of the ballast (120) is greater than a density of a material of the float (110), wherein a density of the separator (100) lies in a value range between a density of the first phase and a density of the second phase of the liquid, thereby causing the center of gravity (SG) of the separator to assume a position at a phase boundary between the first phase and second phase of the liquid during centrifugation; and wherein the sealing edge (112) of the float (110) is formed at a distance (d) greater than zero above the center of gravity (SG) of the separator (100), wherein the float is disk-shaped with a downwardly extending bulge forming a buoyancy body, and wherein the ballast comprises a plurality of circumferentially spaced fingers extending downwardly from an underside of the float, each of the finger having an upper end connected to the float and a free lower end.

2. The separator (100) according to claim 1, wherein the liquid is blood, the first phase is blood serum and the second phase is cruor.

3. The separator (100) according to claim 1, wherein the distance (d) is between 0.05 mm and 4 mm.

4. The separator (100) according to claim 1, wherein the distance (d) is between 1 mm and 3 mm.

5. The separator (100) according to claim 1, wherein the sealing edge (112) extends horizontally in the circumferential direction (R).

6. The separator (100) according to claim 1, wherein the sealing edge (112) extends wave-shaped in the circumferential direction (R) with formation of wave crests (117) and wave troughs (118) and wherein the distance (d) in this case is measured from a deepest wave trough (118) to the center of gravity (SG) of the separator (100).

7. The separator (100) according to claim 1, wherein the float (110) has a spherical deformation.

8. A tubular container, comprising the separator according to claim 1, wherein the separator is detachably clamped in an initial position and wherein the separator is configured to move from the initial position into a sealing position and to rotate by 90° when subjected to a centrifugal force.

9. The separator (100) according to claim 1, wherein the fingers are inwardly curved whereby the upper ends of the fingers are further apart from one another than their lower ends.

\* \* \* \* \*